(12) United States Patent
Stern et al.

(10) Patent No.: US 8,491,912 B2
(45) Date of Patent: Jul. 23, 2013

(54) METHODS OF TREATING OCULAR AND OTHER DISEASES WITH SYN-134R POLYPEPTIDE

(75) Inventors: Michael E. Stern, Mission Viejo, CA (US); Christopher S. Schaumburg, Huntington Beach, CA (US); Karyn F. Siemasko, Anaheim, CA (US); Larry A. Wheeler, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/161,964

(22) Filed: Jun. 16, 2011

(65) Prior Publication Data

US 2011/0318303 A1 Dec. 29, 2011

Related U.S. Application Data

(60) Provisional application No. 61/355,432, filed on Jun. 16, 2010.

(51) Int. Cl.
*A61K 38/20* (2006.01)
*A61K 39/275* (2006.01)
*C07K 14/005* (2006.01)
*C07K 14/065* (2006.01)
*A61K 9/00* (2006.01)
*A61P 27/02* (2006.01)
*A61P 37/00* (2006.01)

(52) U.S. Cl.
USPC .................. 424/184.1; 424/186.1; 424/571; 514/20.8; 530/350; 530/826

(58) Field of Classification Search
None
See application file for complete search history.

(56) References Cited

U.S. PATENT DOCUMENTS

| 4,675,285 A | 6/1987 | Clark et al. |
| 2009/0011979 A1 | 1/2009 | McFadden et al. |

FOREIGN PATENT DOCUMENTS

| WO | WO 9100349 | 6/1990 |
| WO | WO 2007149566 | 6/2007 |
| WO | 2009/074797 | 6/2009 |

OTHER PUBLICATIONS

McCabe, et al, Optometry, Oct. 2009, vol. 80, No. 10, pp. 555-566.*
Lazar et al (Mol. Cell. Biol., 1988, vol. 8, pp. 1247-1252.*
Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, (Current Opinion in Structural Biology 2009, 19: 596-604.*
Stedman's Online Medical Dictionary entries; Jul. 2012; 1 page.*
Volk et al, "IL-10 and its homologs: important immune mediators and emerging immunotherapeutic agents", Trends in Immunology, vol. 22, No. 8, pp. 414-417, Aug. 1, 2001.
Atherton et al., *Solid Phase Peptide Synthesis, a Practical Approach*, I.R.L. Press, Oxford (1989).
Ausubel et al. (eds.), *Current Protocols in Molecular Biology*, Green/Wiley, New York (1987).
Bartlett et al., "A new member of the interleukin 10-related cytokine family encoded by a poxvius", (*J. Gen. Virol.* 85:1401-1412, 2004).
Chen,W. et al. "Conversion of Peripheral $CD4^+CD25^-$ Naïve T Cells to $CD4^+CD25^+$ Regulatory T Cells by TGF-β Induction of Transcription Factor *Foxp3*", 2003. Conversion of peripheral $CD4^+$. *J. Exp. Med.* 198, 1875-1886.
De Paiva et al,2009. << IL-17 disrupts corneal barrier following desiccating stress. *Mucosal Immunol.* 2(3):243-53.
De Paiva, CS. et al. 2007. Dry Eye-Induced Conjunctival Epithelial Squamous Metaplasia Is Modulated by Interferon-{gamma}. *Invest Ophthalmol. Vis. Sci.* 48, 2553-2560.
Evan et al., << Isolation of Monoclonal Antibodies Specific for Human c-myc Proto-Oncogene Product >> , (*Mol Cell Biol* 5:3610-3616, 1985).
Fisher, *Laboratory Techniques In Biochemistry And Molecular Biology*, eds., Work and Burdon, Elsevier, 1980).
Gorelik,L. & Flavell,R.A. 2000. *Abrogation of TGFbeta signaling in T cells leads to spontaneous T cell differentiation and autoimmune disease. Immunity.* 12, 171-181.
Gupta,A. et al. 1996. Transforming growth factor beta-1 and beta-2 in human tear fluid. *Curr. Eye Res.* 15, 605-614.
Hebsgaardet al. , "Splice site prediction in *Arabidopsis thaliana* pre-mRNA by combining local and global sequence information", *Nucleic Acids Res* 1996, 24:3439-3452.
Kaufman et al., "Construction of a Modular Dihydrofolate Reductase cDNA Gene: Analysis of Signals Utilized for Efficient Expression", *Mol. Cell. Biol.*, 2:1304-1319 (1982).
Kunert KS, Tisdale AS, Stern ME, Smith JA, Gipson IK.. 2000. Analysis of topical cyclosporine treatment of patients with dry eye syndrome: effect on conjunctival lymphocytes. *Arch Ophthalmol.* 118(11):1489-96.
Lam H, Bleiden L, de Paiva CS, Farley W, Stern ME, Pflugfelder SC. 2009. Tear cytokine profiles in dysfunctional tear syndrome. *Am J Ophthalmol.* 147(2):198-205.
Lee et al., "The Genome of Yaba-Like Disease Virus, a Yatapoxvirus" (*Virology* 281 :170-192, 2001).
Niederkom et al.,"Desiccating Stress Induces T Cell-Mediated Sjogren's Syndrome-Like Lacrimal Keratoconjunctivitis1" *J Immunol.*, 176(7):3950-7 (2006).
Okayama et al., "A cDNA Cloning Vector That Permits Expression of cDNA Inserts in Mammalian Cells", *Mol. Cell. Biol.*, 3:280-289 (1983).
Sambrook, et al., *Molecular Cloning, A Laboratory Manual*, Cold Spring Harbor Publish., Cold Spring Harbor, N.Y., 2d ed. (1989).
Shen,L., Barabino,S., Taylor,A.W., & Dana,M.R. 2007. Effect of the ocular microenvironment in regulating corneal dendritic cell maturation. *Arch. Ophthalmol.* 125, 908-915.
Siemasko,K.F. et al. In Vitro Expanded CD4+CD25+Foxp3+ Regulatory T Cells Maintain a Normal Phenotype and Suppress Immune-Mediated Ocular Surface Inflammation. 2008. *Invest Ophthalmol. Vis. Sci.* 49(12):5434-40.
Takebe et al., "Structure and Expression of Genes for Surface Proteins in Paramecium", *Mol. Cell. Biol.*, 466-472 (1988).

* cited by examiner

*Primary Examiner* — Bridget E Bunner
*Assistant Examiner* — Fozia Hamud
(74) *Attorney, Agent, or Firm* — Joel B. German; Debra D. Condino

(57) ABSTRACT

Disclosed herein TPV1 is a method of treating ocular and systemic conditions by administering IL-10 and TPV134R polypeptides.

8 Claims, 5 Drawing Sheets

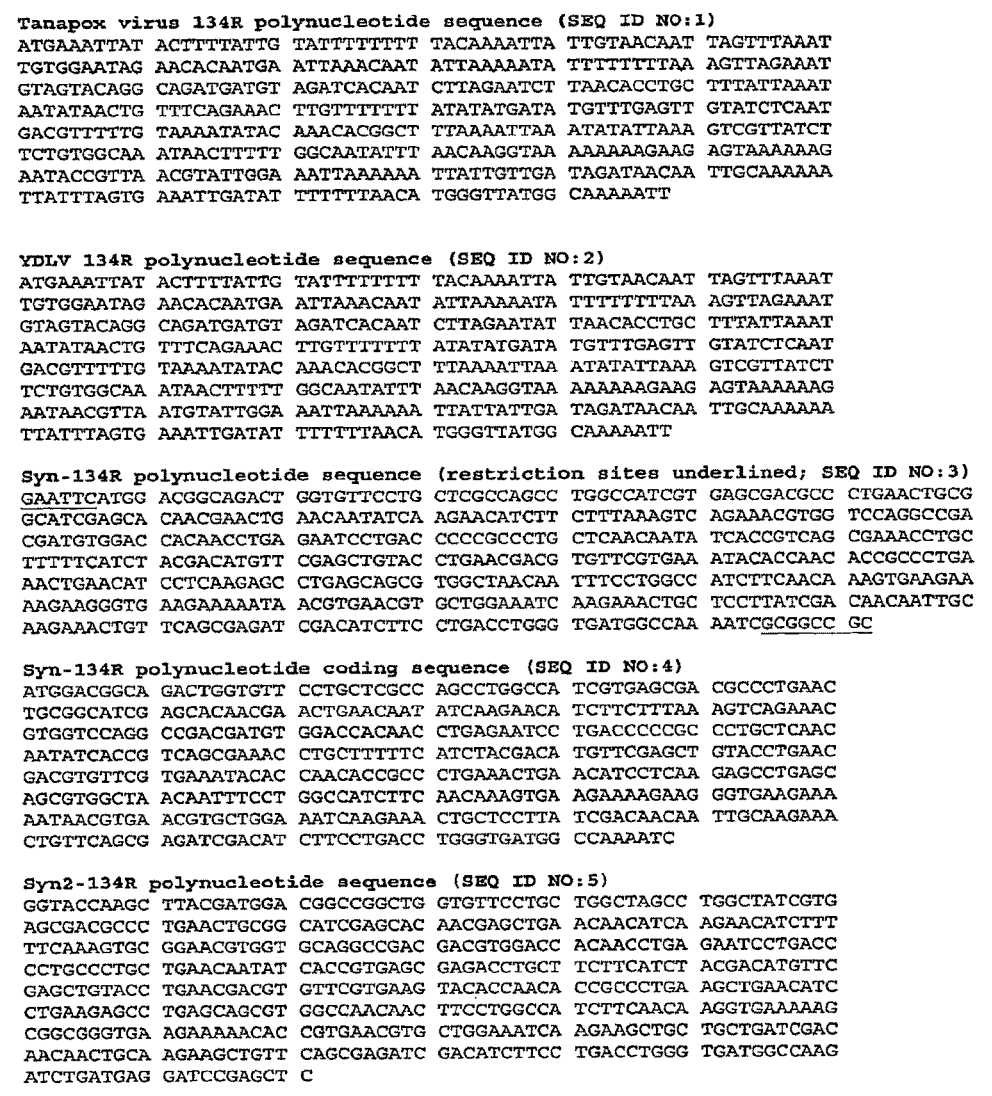

Tanapox virus 134R polynucleotide sequence (SEQ ID NO:1)

```
ATGAAATTAT ACTTTTATTG TATTTTTTTT TACAAAATTA TTGTAACAAT TAGTTTAAAT
TGTGGAATAG AACACAATGA ATTAAACAAT ATTAAAAATA TTTTTTTTAA AGTTAGAAAT
GTAGTACAGG CAGATGATGT AGATCACAAT CTTAGAATCT TAACACCTGC TTTATTAAAT
AATATAACTG TTTCAGAAAC TTGTTTTTTT ATATATGATA TGTTTGAGTT GTATCTCAAT
GACGTTTTTG TAAAATATAC AAACACGGCT TTAAAATTAA ATATATTAAA GTCGTTATCT
TCTGTGGCAA ATAACTTTTT GGCAATATTT AACAAGGTAA AAAAAAGAAG AGTAAAAAAG
AATACCGTTA ACGTATTGGA AATTAAAAAA TTATTGTTGA TAGATAACAA TTGCAAAAAA
TTATTTAGTG AAATTGATAT TTTTTTAACA TGGGTTATGG CAAAAATT
```

YDLV 134R polynucleotide sequence (SEQ ID NO:2)

```
ATGAAATTAT ACTTTTATTG TATTTTTTTT TACAAAATTA TTGTAACAAT TAGTTTAAAT
TGTGGAATAG AACACAATGA ATTAAACAAT ATTAAAAATA TTTTTTTTAA AGTTAGAAAT
GTAGTACAGG CAGATGATGT AGATCACAAT CTTAGAATAT TAACACCTGC TTTATTAAAT
AATATAACTG TTTCAGAAAC TTGTTTTTTT ATATATGATA TGTTTGAGTT GTATCTCAAT
GACGTTTTTG TAAAATATAC AAACACGGCT TTAAAATTAA ATATATTAAA GTCGTTATCT
TCTGTGGCAA ATAACTTTTT GGCAATATTT AACAAGGTAA AAAAAAGAAG AGTAAAAAAG
AATAACGTTA ATGTATTGGA AATTAAAAAA TTATTATTGA TAGATAACAA TTGCAAAAAA
TTATTTAGTG AAATTGATAT TTTTTTAACA TGGGTTATGG CAAAAATT
```

Syn-134R polynucleotide sequence (restriction sites underlined; SEQ ID NO:3)

```
GAATTCATGG ACGGCAGACT GGTGTTCCTG CTCGCCAGCC TGGCCATCGT GAGCGACGCC CTGAACTGCG
GCATCGAGCA CAACGAACTG AACAATATCA AGAACATCTT CTTTAAAGTC AGAAACGTGG TCCAGGCCGA
CGATGTGGAC CACAACCTGA GAATCCTGAC CCCCGCCCTG CTCAACAATA TCACCGTCAG CGAAACCTGC
TTTTTCATCT ACGACATGTT CGAGCTGTAC CTGAACGACG TGTTCGTGAA ATACACCAAC ACCGCCCTGA
AACTGAACAT CCTCAAGAGC CTGAGCAGCG TGGCTAACAA TTTCCTGGCC ATCTTCAACA AAGTGAAGAA
AAGAAGGGTG AAGAAAAATA ACGTGAACGT GCTGGAAATC AAGAAACTGC TCCTTATCGA CAACAATTGC
AAGAAACTGT TCAGCGAGAT CGACATCTTC CTGACCTGGG TGATGGCCAA AATCGCGGCC GC
```

Syn-134R polynucleotide coding sequence (SEQ ID NO:4)

```
ATGGACGGCA GACTGGTGTT CCTGCTCGCC AGCCTGGCCA TCGTGAGCGA CGCCCTGAAC
TGCGGCATCG AGCACAACGA ACTGAACAAT ATCAAGAACA TCTTCTTTAA AGTCAGAAAC
GTGGTCCAGG CCGACGATGT GGACCACAAC CTGAGAATCC TGACCCCCGC CCTGCTCAAC
AATATCACCG TCAGCGAAAC CTGCTTTTTC ATCTACGACA TGTTCGAGCT GTACCTGAAC
GACGTGTTCG TGAAATACAC CAACACCGCC CTGAAACTGA ACATCCTCAA GAGCCTGAGC
AGCGTGGCTA ACAATTTCCT GGCCATCTTC AACAAAGTGA AGAAAAGAAG GGTGAAGAAA
AATAACGTGA ACGTGCTGGA AATCAAGAAA CTGCTCCTTA TCGACAACAA TTGCAAGAAA
CTGTTCAGCG AGATCGACAT CTTCCTGACC TGGGTGATGG CCAAAATC
```

Syn2-134R polynucleotide sequence (SEQ ID NO:5)

```
GGTACCAAGC TTACGATGGA CGGCCGGCTG GTGTTCCTGC TGGCTAGCC TGGCTATCGTG
AGCGACGCCC TGAACTGCGG CATCGAGCAC AACGAGCTGA ACAACATCA AGAACATCTTT
TTCAAAGTGC GGAACGTGGT GCAGGCCGAC GACGTGGACC ACAACCTGA GAATCCTGACC
CCTGCCCTGC TGAACAATAT CACCGTGAGC GAGACCTGCT TCTTCATCT ACGACATGTTC
GAGCTGTACC TGAACGACGT GTTCGTGAAG TACACCAACA CCGCCCTGA AGCTGAACATC
CTGAAGAGCC TGAGCAGCGT GGCCAACAAC TTCCTGGCCA TCTTCAACA AGGTGAAAAAG
CGGCGGGTGA AGAAAAACAC CGTGAACGTG CTGGAAATCA AGAAGCTGC TGCTGATCGAC
AACAACTGCA AGAAGCTGTT CAGCGAGATC GACATCTTCC TGACCTGGG TGATGGCCAAG
ATCTGATGAG GATCCGAGCT C
```

Figure 1A

Syn2-134R polynucleotide coding sequence (SEQ ID NO:6)
ATGGACGGCC GGCTGGTGTT CCTGCTGGCT AGCCTGGCTA TCGTGAGCGA CGCCCTGAAC
TGCGGCATCG AGCACAACGA GCTGAACAAC ATCAAGAACA TCTTTTTCAA AGTGCGGAAC
GTGGTGCAGG CCGACGACGT GGACCACAAC CTGAGAATCC TGACCCCTGC CCTGCTGAAC
AATATCACCG TGAGCGAGAC CTGCTTCTTC ATCTACGACA TGTTCGAGCT GTACCTGAAC
GACGTGTTCG TGAAGTACAC CAACACCGCC CTGAAGCTGA ACATCCTGAA GAGCCTGAGC
AGCGTGGCCA ACAACTTCCT GGCCATCTTC AACAAGGTGA AAAGCGGCG GGTGAAGAAA
AACACCGTGA ACGTGCTGGA AATCAAGAAG CTGCTGCTGA TCGACAACAA CTGCAAGAAG
CTGTTCAGCG AGATCGACAT CTTCCTGACC TGGGTGATGG CCAAGATCTG ATGA Tanapox virus 134R polypeptide sequence (SEQ ID NO:7)
MKLYFYCIFF YKIIVTISLN CGIEHNELNN IKNIFFKVRN VVQADDVDHN LRILTPALLN
NITVSETCFF IYDMFELYLN DVFVKYTNTA LKLNILKSLS SVANNFLAIF NKVKKRRVKK
NTVNVLEIKK LLLIDNNCKK LFSEIDIFLT WVMAKI YDLV 134R polypeptide sequence (SEQ ID NO:8)
MKLYFYCIFF YKIIVTISLN CGIEHNELNN IKNIFFKVRN VVQADDVDHN LRILTPALLN
NITVSETCFF IYDMFELYLN DVFVKYTNTA LKLNILKSLS SVANNFLAIF NKVKKRRVKK
NNVNVLEIKK LLLIDNNCKK LFSEIDIFLT WVMAKI Syn-134R polypeptide sequence (SEQ ID NO:9)
MDGRLVFLLA SLAIVSDALN CGIEHNELNN IKNIFFKVRN VVQADDVDHN LRILTPALLN
NITVSETCFF IYDMFELYLN DVFVKYTNTA LKLNILKSLS SVANNFLAIF NKVKKRRVKK
NNVNVLEIKK LLLIDNNCKK LFSEIDIFLT WVMAKI Syn2-134R polypeptide sequence (SEQ ID NO:10)
MDGRLVFLLA SLAIVSDALN CGIEHNELNN IKNIFFKVRN VVQADDVDHN LRILTPALLN
NITVSETCFF IYDMFELYLN DVFVKYTNTA LKLNILKSLS SVANNFLAIF NKVKKRRVKK
NTNVNVLEIKK LLLIDNNCKK LFSEIDIFLT WVMAKI

Figure 1B myxoma virus M-T7 polypeptide sequence (SEQ ID NO:11)
MDGRLVFLLA SLAIVSDAVR LTSYDLNTFV TWQDDGYTYN VSIKPYTTAT WINVCEWASS
SCNVSLALQY DLDVVSWARL TRVGKYTEYS LEPTCAVARF SPPEVQLVRT GTSVEVLVRH
PVVYLRGQEV SVYGHSFCDY DFGYKTIFLF SKNKRAEYVV PGRYCDNVEC RFSIDSQESV
CATAVLTYGD SYRSEAGVEV CVPELAKREV SPYIVKKSSD LEYVKRAIHN EYRLDTSSEG
RRLEELYLTV ASMFERLVED VFE myxoma virus M-T7 polypeptide signal sequence (SEQ ID NO:12)
MDGRLVFLLA SLAIVSDA

Figure 2

SEQUENCE LISTING

```
<160> NUMBER OF SEQ ID NOS: 12

<210> SEQ ID NO 1
<211> LENGTH: 468
<212> TYPE: DNA
<213> ORGANISM: Unknown
<220> FEATURE:
<223> OTHER INFORMATION: Tanaprox

<400> SEQUENCE: 1
atgaaattat acttttattg tattttttt tacaaaatta ttgtaacaat tagtttaaat     60
tgtggaatag aacacaatga attaaacaat attaaaaata ttttttttaa agttagaaat    120
gtagtacagg cagatgatgt agatcacaat cttagaatct taacacctgc tttattaaat    180 aataactg tttcagaaac ttgttttttt atatatgata tgtttgagtt gtatctcaat      240 gacgttttg taaaatatac aaacacggct ttaaaattaa atatattaaa gtcgttatct    300
tctgtggcaa ataacttttt ggcaatattt aacaaggtaa aaaaagaag agtaaaaaag    360 aataccgtta acgtattgga aattaaaaaa ttattgttga tagataacaa ttgcaaaaaa    420
ttatttagtg aaattgatat ttttttaaca tgggttatgg caaaaatt                 468

<210> SEQ ID NO 2
<211> LENGTH: 467
<212> TYPE: DNA
<213> ORGANISM: Unknown
<220> FEATURE:
<223> OTHER INFORMATION: Yaba Disease Like

<400> SEQUENCE: 2
atgaaattat acttttattg tattttttt tacaaaatta ttgtaacaat tagtttaaat     60
tgtggaatag aacacaatga attaaacaat attaaaaata ttttttttaa agttagaaat    120
gtagtacagg cagatgatgt agatcacaat cttagaatat taacacctgc tttattaaat    180 aataactg tttcagaaac ttgtttttta tatatgatat gtttgagttg tatctcaatg      240 acgttttgt aaaatataca aacacggctt taaaattaaa tatattaaag tcgttatctt    300
ctgtggcaaa taacttttg gcaatattta acaaggtaaa aaaagaaga gtaaaaaaga    360 ataacgttaa tgtattggaa attaaaaaat tattattgat agataacaat tgcaaaaaat    420
tatttagtga aattgatatt tttttaacat gggttatggc aaaaatt                  467

<210> SEQ ID NO 3
```

```
<211> LENGTH: 482
<212> TYPE: DNA
<213> ORGANISM: Unknown
<220> FEATURE:
<223> OTHER INFORMATION: Syn-134R

<400> SEQUENCE: 3
gaattcatgg acggcagact ggtgttcctg ctcgccagcc tggccatcgt gagcgacgcc      60
ctgaactgcg gcatcgagca caacgaactg aacaatatca gaacatcttc ctttaaagtc     120
agaaacgtgg tccaggccga cgatgtggac cacaacctga atcctgac ccccgccctg      180 ctcaacaata tcaccgtcag cgaaacctgc tttttcatct acgacatgtt cgagctgtac     240
ctgaacgacg tgttcgtgaa atacaccaac accgccctga actgaacat cctcaagagc     300 ctgagcagcg tggctaacaa tttcctggcc atcttcaaca agtgaagaa agaagggtg      360 aagaaaaata cgtgaacgt gctggaaatc aagaaactgc tccttatcga caacaattgc     420
aagaaactgt tcagcgagat cgacatcttc ctgacctggg tgatggccaa atcgcggcc     480 gc                                                                   482

<210> SEQ ID NO 4
<211> LENGTH: 468
<212> TYPE: DNA
<213> ORGANISM: Unknown
<220> FEATURE:
<223> OTHER INFORMATION: Syn-134R

<400> SEQUENCE: 4
atggacggca gactggtgtt cctgctcgcc agcctggcca tcgtgagcga cgccctgaac      60
tgcggcatcg agcacaacga actgaacaat atcaagaaca tcttcttta agtcagaaac     120 gtggtccagg ccgacgatgt ggaccacaac ctgagaatcc tgaccccgc cctgctcaac      180 aatatcaccg tcagcgaaac ctgcttttc atctacgaca tgttcgagct gtacctgaac     240
gacgtgttcg tgaaatacac caacaccgcc ctgaactga catcctcaa gagcctgagc     300 agcgtggcta acaatttcct ggccatcttc aacaaagtga agaaagaag ggtgaagaaa     360 aataacgtga acgtgctgga aatcaagaaa ctgctcctta tcgacaacaa ttgcaagaaa     420
ctgttcagcg agatcgacat cttcctgacc tgggtgatgg ccaaaatc                468

<210> SEQ ID NO 5
<211> LENGTH: 501
<212> TYPE: DNA
<213> ORGANISM: Unknown
<220> FEATURE:
<223> OTHER INFORMATION: Syn2-134R

<400> SEQUENCE: 5
ggtaccaagc ttacgatgga cggccggctg gtgttcctgc tggctagcct ggctatcgtg      60
agcgacgccc tgaactgcgg catcgagcac aacgagctga acaacatcaa gaacatcttt     120
ttcaaagtgc ggaacgtggt gcaggccgac gacgtggacc acaacctgag aatcctgacc     180
cctgccctgc tgaacaatat caccgtgagc gagacctgct tcttcatcta cgacatgttc     240 agctgtacc tgaacgacgt gttcgtgaag tacaccaaca ccgccctgaa gctgaacatc     300
ctgaagagcc tgagcagcgt ggccaacaac ttcctggcca tcttcaacaa ggtgaaaaag     360
cggcgggtga agaaaaacac cgtgaacgtg ctggaaatca gaagctgct gctgatcgac     420 aacaactgca gaagctgtt cagcgagatc gacatcttcc tgacctgggt gatggccaag     480
atctgatgag gatccgagct c                                              501
```

<210> SEQ ID NO 6
<211> LENGTH: 474
<212> TYPE: DNA
<213> ORGANISM: Unknown
<220> FEATURE:
<223> OTHER INFORMATION: Syn2-134R

<400> SEQUENCE: 6

```
atggacggcc ggctggtgtt cctgctggct agcctggcta tcgtgagcga cgccctgaac      60
tgcggcatcg agcacaacga gctgaacaac atcaagaaca tcttttttcaa agtgcggaac     120
gtggtgcagg ccgacgacgt ggaccacaac ctgagaatcc tgaccccctgc cctgctgaac    180
aatatcaccg tgagcgagac ctgcttcttc atctacgaca tgttcgagct gtacctgaac     240
gacgtgttcg tgaagtacac caacaccgcc ctgaagctga catcctgaa gagcctgagc      300
agcgtggcca caacttcct ggccatcttc aacaaggtga aaaagcggcg ggtgaagaaa      360
aacaccgtga acgtgctgga atcaagaag ctgctgctga tcgacaacaa ctgcaagaag     420
ctgttcagcg agatcgacat cttcctgacc tgggtgatgg ccaagatctg atga           474
```

<210> SEQ ID NO 7
<211> LENGTH: 156
<212> TYPE: PRT
<213> ORGANISM: Unknown
<220> FEATURE:
<223> OTHER INFORMATION: Tanapox

<400> SEQUENCE: 7

```
Met Lys Leu Tyr Phe Tyr Cys Ile Phe Phe Tyr Lys Ile Ile Val Thr
 1               5                  10                  15

Ile Ser Leu Asn Cys Gly Ile Glu His Asn Glu Leu Asn Asn Ile Lys

```
                    20                  25                  30
Asn Ile Phe Phe Lys Val Arg Asn Val Val Gln Ala Asp Asp Val Asp
                35                  40                  45

His Asn Leu Arg Ile Leu Thr Pro Ala Leu Leu Asn Asn Ile Thr Val
            50                  55                  60

Ser Glu Thr Cys Phe Phe Ile Tyr Asp Met Phe Glu Leu Tyr Leu Asn
65                  70                  75                  80

Asp Val Phe Val Lys Tyr Asn Thr Ala Leu Lys Leu Asn Ile Leu Lys
                85                  90                  95

Ser Leu Ser Ser Val Ala Asn Asn Phe Leu Ala Ile Phe Asn Lys Val
            100                 105                 110

Lys Lys Arg Arg Val Lys Lys Asn Asn Val Asn Val Leu Glu Ile Lys
            115                 120                 125

Lys Leu Leu Leu Ile Asp Asn Asn Cys Lys Lys Leu Phe Ser Glu Ile
            130                 135                 140

Asp Ile Leu Phe Leu Thr Trp Val Met Ala Lys Ile
145                 150                 155

<210> SEQ ID NO 9
<211> LENGTH: 158
<212> TYPE: PRT
<213> ORGANISM: Unknown
<220> FEATURE:
<223> OTHER INFORMATION: Syn-134R

<400> SEQUENCE: 9

Met Asp Gly Arg Leu Val Phe Leu Leu Ala Ser Leu Ala Ile Val Ser
1               5                   10                  15

Asp Ala Leu Asn Cys Gly Ile Glu His Asn Glu Leu Asn Asn Ile Lys
            20                  25                  30

Asn Ile Phe Phe Lys Val Arg Asn Val Val Gln Ala Asp Asp Val Asp
                35                  40                  45

His Asn Leu Arg Ile Leu Thr Pro Ala Leu Leu Asn Asn Ile Thr Val
            50                  55                  60

Ser Glu Thr Cys Phe Phe Ile Tyr Asp Met Phe Glu Leu Tyr Leu Asn
65                  70                  75                  80

Asp Val Phe Val Lys Tyr Thr Asn Thr Ala Leu Lys Leu Asn Ile Leu
                85                  90                  95

Lys Ser Leu Ser Ser Val Ala Asn Asn Phe Leu Ala Ile Phe Asn Leu
            100                 105                 110

Cys Val Lys Ile Cys Arg Arg Val Lys Lys Asn Asn Val Asn Val Leu
            115                 120                 125

Glu Ile Lys Lys Leu Leu Leu Ile Asp Asn Asn Cys Lys Lys Leu Phe
            130                 135                 140

Ser Glu Ile Asp Ile Phe Leu Thr Trp Val Met Ala Lys Ile
145                 150                 155

<210> SEQ ID NO 10
<211> LENGTH: 157
<212> TYPE: PRT
<213> ORGANISM: Unknown
<220> FEATURE:
<223> OTHER INFORMATION: Syn-134R

<400> SEQUENCE: 10

Met Asp Gly Arg Leu Val Phe Leu Leu Ala Ser Leu Ala Ile Val Ser
1               5                   10                  15

Asp Ala Leu Asn Cys Gly Ile Glu His Asn Glu Leu Asn Asn Ile Lys
```

```
            20                  25                  30
Asn Ile Phe Phe Lys Val Arg Asn Val Val Gln Ala Asp Asp Val Asp
                35                  40                  45

His Asn Leu Arg Ile Leu Thr Pro Ala Leu Leu Asn Asn Ile Thr Val
 50                  55                  60

Ser Glu Thr Cys Phe Phe Ile Tyr Asp Met Phe Glu Leu Tyr Leu Asn
65                  70                  75                  80

Asp Val Phe Val Lys Tyr Thr Asn Thr Ala Leu Lys Leu Asn Ile Leu
                85                  90                  95

Lys Ser Leu Ser Ser Val Ala Asn Asn Phe Leu Ala Ile Phe Asn Lys
                100                 105                 110

Val Lys Lys Arg Arg Val Lys Lys Asn Thr Asn Val Asn Val Leu Glu
                115                 120                 125

Ile Lys Lys Leu Leu Leu Ile Asp Asn Asn Cys Lys Lys Leu Phe Ser
                130                 135                 140

Glu Ile Asp Ile Phe Leu Thr Trp Val Met Ala Lys Ile
145                 150                 155

<210> SEQ ID NO 11
<211> LENGTH: 263
<212> TYPE: PRT
<213> ORGANISM: Unknown
<220> FEATURE:
<223> OTHER INFORMATION: myxoma

<400> SEQUENCE: 11

Met Asp Gly Arg Leu Val Phe Leu Leu Ala Ser Leu Ala Ile Val Ser
 1               5                  10                  15

Asp Ala Val Arg Leu Thr Ser Tyr Asp Leu Asn Thr Phe Val Thr Trp
                20                  25                  30

Gln Asp Asp Gly Tyr Thr Tyr Asn Val Ser Ile Lys Pro Tyr Thr Thr
                35                  40                  45

Ala Thr Trp Ile Asn Val Cys Glu Trp Ala Ser Ser Ser Cys Asn Val
 50                  55                  60

Ser Leu Ala Leu Gln Tyr Asp Leu Asp Val Val Ser Trp Ala Arg Leu
65                  70                  75                  80

Thr Arg Val Gly Lys Tyr Thr Glu Tyr Ser Leu Glu Pro Thr Cys Ala
                85                  90                  95

Val Ala Arg Phe Ser Pro Pro Glu Val Gln Leu Val Arg Thr Gly Thr
                100                 105                 110

Ser Val Glu Val Leu Val Arg His Pro Val Val Tyr Leu Arg Gly Gln
                115                 120                 125

Glu Val Ser Val Tyr Gly His Ser Pro Cys Tyr Asp Phe Gly Tyr
                130                 135                 140

Lys Thr Ile Phe Leu Phe Ser Lys Asn Lys Arg Ala Glu Tyr Val Val
145                 150                 155                 160

Pro Gly Arg Tyr Cys Asp Asn Val Glu Cys Arg Pro Ser Ile Asp Ser
                165                 170                 175

Gln Glu Ser Val Cys Ala Thr Ala Val Leu Thr Tyr Gly Asp Ser Tyr
                180                 185                 190

Arg Ser Glu Ala Gly Val Glu Val Cys Val Pro Glu Leu Ala Lys Arg
                195                 200                 205

Glu Val Ser Pro Tyr Ile Val Lys Lys Ser Asp Leu Glu Tyr Val
                210                 215                 220

Lys Arg Ala Ile His Asn Glu Tyr Arg Leu Asp Thr Ser Ser Glu Gly
225                 230                 235                 240
```

```
Arg Arg Leu Glu Glu Leu Tyr Leu Thr Val Ala Ser Met Phe Glu Arg
                245                 250                 255
Leu Val Glu Asp Val Phe Glu
            260

<210> SEQ ID NO 12
<211> LENGTH: 18
<212> TYPE: PRT
<213> ORGANISM: Unknown
<220> FEATURE:
<223> OTHER INFORMATION: myxoma

<400> SEQUENCE: 12

Met Asp Gly Arg Leu Val Phe Leu Leu Ala Ser Leu Ala Ile Val Ser
1               5                   10                  15

Asp Ala
```

METHODS OF TREATING OCULAR AND OTHER DISEASES WITH SYN-134R POLYPEPTIDE

CROSS REFERENCE

This application claims the benefit of U.S. Provisional Patent Application Ser. No. 61/355,432, filed on Jun. 16, 2010, the entire disclosure of which is incorporated herein by this specific reference.

Disclosed herein are methods for treating ocular diseases, such as keratoconjunctivitis sicca, ocular cicatricial pemphigoid, blepharitis, ocular allergy, ocular infection, and diminished corneal sensitivity, and for treating systemic diseases, such as Stevens-Johnson disease and graft versus host disease, by administering to a subject interleukin 10 or TPV 134R Polypeptides.

BRIEF DESCRIPTION OF THE DRAWINGS

FIG. 1A shows the Tanapox virus TPV 134R polynucleotide sequence (SEQ ID NO:1), the YLDV 134R polynucleotide sequence (SEQ ID NO:2), the Syn-134R polynucleotide sequence (with restriction sites underlined; SEQ ID NO:3), the Syn-134R polynucleotide coding sequence (SEQ ID NO:4), and the Syn2-134R polynucleotide sequence (SEQ ID NO:5).

FIG. 1B shows the Syn2-134R polynucleotide coding sequence (SEQ ID NO:6), the Tanapox virus 134R polypeptide sequence (SEQ ID NO:7), the YLDV 134R polypeptide sequence (SEQ ID NO: 8), the Syn-134R polypeptide sequence (SEQ ID NO:9) and the Syn2-134R polypeptide sequence (SEQ ID NO: 10).

FIG. 2 shows the myxoma virus M-T7 polypeptide sequence (SEQ ID NO:11) and the myxoma virus M-T7 polypeptide signal sequence (SEQ ID NO: 12).

FIG. 3 shows that topical treatment with IL-10 attenuated CD4+ T cell activation following exposure to desiccating stress. Experimental dry eye was induced in mice treated vehicle (PBS) or recombinant IL-10. After 5 days of desiccating stress CD4+ T cells were isolated and $5\times10^6$ cells were adoptively transferred into nude recipient mice to evaluate the effect of IL-10 treatment on autoreactive T cell activation. Nude recipients of CD4+ T cells from mice exposed to desiccating stress in the presence of rIL-10 displayed a significant reduction in the number of infiltrating CD4+ T cells within the ocular surface tissues (Lid, meibomian gland—MG, conjunctiva—conj). By contrast, mice receiving only vehicle (PBS) showed marked accumulation of CD4+ T cells.

FIG. 4 shows that topical treatment with IL-10 preserved Goblet cells in nude recipient mice. Experimental dry eye was induced in mice treated vehicle (PBS) or recombinant IL-10. After 5 days of desiccating stress CD4+ T cells were isolated and $5\times10^6$ cells were adoptively transferred into nude recipient mice to evaluate the effect of IL-10 treatment on Goblet cells density. Nude recipients of CD4+ T cells from mice exposed to desiccating stress in the presence of rIL-10 displayed a significant preservation of the total number of Goblet cells within the conjunctiva; however, mice receiving vehicle alone displayed a dramatic loss of Goblet cells.

DETAILED DESCRIPTION OF THE INVENTION

IL-10

IL-10 is a cytokine capable of mediating a number of actions or effects. IL-10 has been isolated from both mouse and human cells and is involved in controlling the immune responses of different classes or subsets of T helper (Th) cells. Th cells can be divided into different subsets that are distinguished by their cytokine production profiles. Th1 T cell clones produce interleukin-2 (IL-2) and interferon-γ (IFN-γ) whereas Th2 cell clones secrete IL-10, IL-4, and IL-5, generally following activation by antigens or mitogenic lectins. Both classes of Th cell clones produce cytokines such as tumor necrosis factor-α (TNF-α), IL-3, and granulocyte-macrophage colony stimulating factor (GM-CSF). A third category of Th cells (Th0) produces IL-2, IFN-γ, IL-4, IL-5, TNF-α, IL-3, and GM-CSF simultaneously.

IL-10 suitable for use in the invention can be obtained from a number of sources. For example, it can be isolated from culture media of activated T-cells capable of secreting the protein. Additionally, the polypeptide or active fragments thereof can be chemically synthesized using standard techniques as known in the art. See, e.g., Merrifield, *Science* 233:341-47 (1986) and Atherton et al., *Solid Phase Peptide Synthesis, a Practical Approach*, I.R.L. Press, Oxford (1989).

Preferably, the protein or polypeptide is obtained by recombinant techniques using isolated nucleic acids encoding for the IL-10 polypeptide. General methods of molecular biology and described, e.g., in Sambrook, et al., *Molecular Cloning, A Laboratory Manual*, Cold Spring Harbor Publish., Cold Spring Harbor, N.Y., 2d ed. (1989) and Ausubel et al. (eds.), Current Protocols in Molecular Biology, Green/Wiley, New York (1987 and periodic supplements). The appropriate sequences can be obtained using standard techniques from either genomic or cDNA libraries. Libraries are constructed from nucleic acid extracted from the appropriate cells. See, e.g., example, WO 9100349, the contents of which are incorporated herein by reference, which discloses recombinant methods to make IL-10. Useful gene sequences can be found, e.g., in various sequence databases, e.g., Gen Bank and EMBL for nucleic acid, and PIR and Swiss-Prot for protein, c/o Intelligenetics, Mountain View, Calif.; or the Genetics Computer Group, University of Wisconsin Biotechnology Center, Madison, Wis.

Clones comprising sequences that encode human-IL-10 have been deposited with the American Type Culture Collection (ATCC), Rockville, Md. under the Accession Numbers 68191 and 68192. Identification of clones harboring the sequences encoding IL-10 is performed by either nucleic acid hybridization or immunological detection of the encoded protein, if an expression vector is used. Oligonucleotide probes based on the deposited sequences disclosed in WO 9100349 are particularly useful. Oligonucleotide probes useful for identification of the sequences can also be prepared from conserved regions of related genes in other species. Alternatively, degenerate probes based on the amino acid sequence of IL-10 can be used.

Standard transfection methods can be used to produce prokaryotic, mammalian, yeast or insect cell lines which express large quantities of the polypeptide. Exemplary *E. coli* strains suitable for both expression and cloning include W3110 (ATCC No. 27325), JA221, C600, ED767, DH1, LE392, HB101, X1776 (ATCC No. 31244), X2282, RR1 (ATCC No. 31343). Exemplary mammalian cell lines include COS-7 cells, mouse L cells and CHO cells.

Various expression vectors can be used to express the gene. Conventional vectors used for expression of recombinant proteins in prokaryotic or eukaryotic cells may be used. Vectors include the pcD vectors described in Okayama et al., *Mol. Cell. Biol.,* 3:280-289 (1983); and Takebe et al., *Mol. Cell. Biol.,* 466-472 (1988). Other SV40-based mammalian expression vectors include those disclosed in Kaufman et al., *Mol. Cell. Biol.,* 2:1304-1319 (1982) and U.S. Pat. No. 4,675, 285, both of which are incorporated herein by reference. These SV40-based vectors are particularly useful in COS7 monkey cells (ATCC No. CRL 1651), as well as other mammalian cells such as mouse L cells. See also, Pouwels et al. (1989 and supplements) Cloning Vectors: A Laboratory Manual, Elsevier, N.Y.

Figure 3:
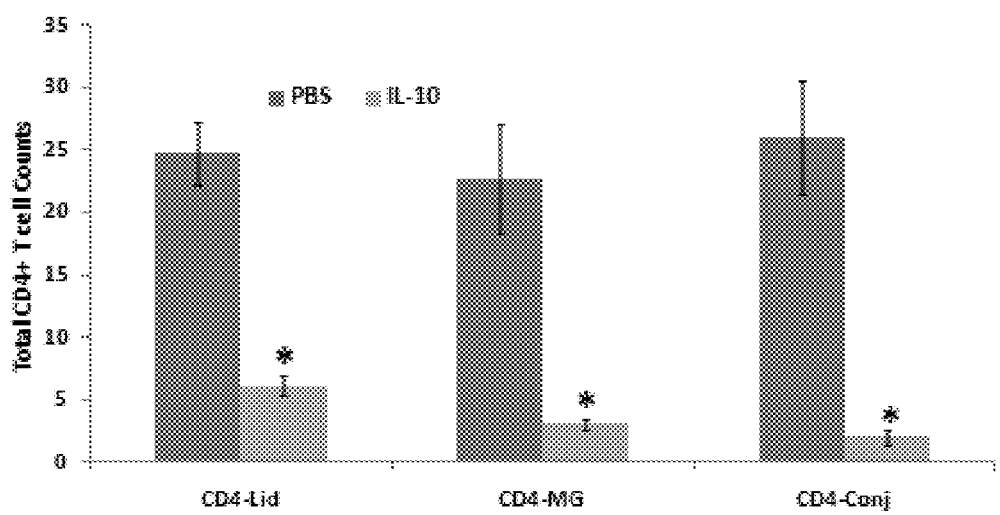

Peptides of the invention may be expressed in soluble form such as a secreted product of a transformed yeast or mammalian cell. In this situation, the peptide can be purified according to standard procedures well known in the art. For example, purification steps could include ammonium sulfate precipitation, ion exchange chromatography, gel filtration, electrophoresis, affinity chromatography, and the like.

Alternatively, IL-10 may be expressed in insoluble form such as aggregates or inclusion bodies. These peptides are purified as described herein, or by standard procedures known in the art. Examples of purification steps include separating the inclusion bodies from disrupted host cells by centrifugation, solubilizing the inclusion bodies with chaotropic agents and reducing agents, diluting the solubilized mixture, and lowering the concentration of chaotropic agent and reducing agent so that the peptide assumes a biologically active conformation.

The nucleotide sequences used to transfect the host cells can be modified according to standard techniques to yield IL-10 polypeptides or fragments thereof, with a variety of desired properties. IL-10 polypeptides can be readily designed and manufactured utilizing various recombinant DNA techniques, including these well known to those skilled in the art.

In one embodiment, IL-10 is produced in E. coli as inclusion bodies which are isolated by lysing the E. coli cell and centrifuging the resultant supernatant at about 13,000 g. The resultant pellet is collected and washed by homogenizing in an appropriate buffer to remove contaminant proteins. The inclusion bodies are solubilized in a suitable buffer containing 6 molar (M) guanidine hydrochloric acid (HCl) and 10 millimolar (mM) dithiothreitol (DTT) in the proportion of 10 ml buffer per gram of inclusion bodies. The mixture is incubated at 4° C. for 3 hours. After 3 hours, the solubilized inclusion bodies are diluted 100 fold with buffer containing 0.5M guanidine HCl, reduced glutathione, and oxidized glutathione in a ratio of 2:1 and protease inhibitors at pH 8.5, and allowed to refold for 18 hours at 4° C. in the presence of a nitrogen atmosphere. The refolded material is filtered and solid diammonium sulfate ($(NH_4)_2SO_4$) is added to make the final concentration 25%. The material is loaded onto a hydrophilic interaction column using phenyl sepharose, butyl sepharose or toyo pearl. The column is washed with 10 bed volumes of 25% $(NH_4)_2SO_4$ in buffer (TRIS 30 mM, $(NH_4)_2SO_4$ at 25% saturation, and tetra sodium EDTA 10 mM at pH 8.5) and eluted with a buffer containing no diammonium sulfate (TRIS 30 mM, NaCl 30 mM, and tetra sodium EDTA 10 mM at pH 8.5). The eluate peak fractions are collected, assayed, analysed and pooled. The pools are adjusted to pH 9.0 and conductivity 5.0 mhos. The pools are loaded onto a Q Sepharose column and the flow is collected. This flow-through contains the active fraction of mIL-10. The material that is bound to the column contains inactive mIL-10 and is eluted with 1.0M sodium chloride (NaCl). The active fractions are pooled, analysed, assayed and adjusted to pH 7.0 and conductivity 5.0-6.0 mhos. The material is loaded onto an S-Sepharose column. The flow-through fractions are collected. The column is washed with 10 bed volumes of 20M HEPES (N-[2-hydroxyethyl]piperazine-N-[2-ethanesulfonic acid]) pH 7.0, which is the equilibration buffer. The column is eluted with a NaCl gradient from 0-6M. The peak fractions are pooled and analysed, and contain active, 95% pure, mIL-10. The purified mIL-10 is stored at 4° C. under sterile aseptic conditions. The final product has pyrogen levels of less than 0.1 endotoxin units (EU)/ml.

IL-10 can also be synthesized in solid or liquid phase as is known in the art. Peptides can be synthesized at different substitution levels and the synthesis may follow a stepwise format or a coupling approach. The stepwise method includes condensing amino acids to the terminal amino group sequentially and individually. The coupling, or segment condensation, approach involves coupling fragments divided into several groups to the terminal amino acid. Synthetic methods include azide, chloride, acid anhydride, mixed anhydride, active ester, Woodward reagent K, and carbodiimidazole processes as well as oxidation-reduction and other processes. The synthetic peptides are usually purified by a method such as gel filtration chromatography or high performance liquid chromatography.

In one embodiment, one can use in the method of the invention the polypeptides described in WO 2007149566 and US 2009/0011979, the entire contents of both of which are incorporated herein by reference. Those references describe proteins encoded by genes for the Tanapox virus (TPV) and Yaba Like Disease Virus (YLDV). TPV and TLDV are members of the genus *Yatapoxvirus*, which infects simians and other primates including humans. Nucleotide sequences of TPV and YLDV are over 98% identical and TPV and YLDV are serologically cross-reactive.

The YLDV 134R gene encodes a protein homologous to cellular proteins of the IL-10 family. This protein was described by Lee et al. (Virology 281:170-192, 2001) and Bartlett et al. (J. Gen. Virol. 85:1401-1412, 2004).

In one embodiment, one can use a substantially pure polypeptide including at least a fragment of TPV134R. The polypeptide may be biologically active (e.g., have a greater activity in a cell, as measured by STAT3 phosphorylation, as compared to human IL-10). The polypeptide may be expressed in a host cell. The polypeptide may be secreted from a mammalian host cell. At least a portion of the amino acid sequence (e.g., the entire amino acid sequence) of the polypeptide may be at least 60% (e.g., 70%, 80%, 90%, 91%, 92%, 93%, 94%, 95%, 96%, 97%, 98%, 99%, or 100%) identical to amino acids 19-156 of TPV134R (SEQ ID NO:7). The polypeptide may further include a heterologous signal sequence (e.g., the amino acid sequence MDGRL VFLLASLAIVSDA (SEQ ID NO: 12)). The signal sequence may be an N-terminal or C-terminal sequence. In other embodiments, the polypeptide comprises or consists essentially of the amino acid sequence of SEQ ID NO: 9 or 10, or a polypeptide that is at least 90%, 91%, 92%, 93%, 94%, 95%, 96%, 97%, 98%, 99%, or 100% identical to SEQ ID NO: 9 or 10.

In one embodiment, one can use a polypeptide which further comprises a heterologous signal sequence (e.g., an N-terminal or C-terminal signal sequence such as MDGRLV-FLLASLAIVSDA (SEQ ID NO:12)).

In another embodiment, one can use a fusion protein compound a myxoma T7 signal sequence and a heterologous sequence. The signal sequence may include MDGRLV-FLLASLAIVSDA (SEQ ID NO: 12) or any variant thereof (e.g., those described herein).

By "134R protein," the inventors mean a protein having substantial identity to the Tanapox 134R amino acid sequence (SEQ ID NO:7) or Yaba-Like Disease Virus (YLDV) 134R amino acid sequence (SEQ ID NO: 8). SEQ ID NO: 8 describes the naturally occurring YLDV 134R sequence; amino acids 1412-2004 encode a naturally occurring truncated form.

In one embodiment, one can use in the method of the invention 134R proteins, functional fragments thereof, and chimeric variants thereof (e.g., including a heterologous signal sequence), and fusion proteins with a myxoma T7 signal sequence (such polypeptides, functional fragments, chimeric variants, and fusion proteins are referred to as "TPV Polypeptides").

Tanapox 134R (TPV134R) (SEQ ID NOS: 1 and 7; FIGS. 1A and 1B) and Yaba Like Disease Virus (YLDV134R) (SEQ ED NOS:2 and 8) are homologs of human IL-10 and are related to the IL-10 family of glycoproteins which include IL-10, IL-19, IL-20, IL-24, and IL-26.

In one embodiment, one can modify the TPV Polypeptides by incorporating any signal sequence known in the art, e.g., those described in the database described by Choo at al. (BMC Bioinformatics 2005, 6:249, 2005; available from the National University of Singapore). In some embodiments, the protein is modified to incorporate a signal peptide that increases secretion of the protein from a cell. When the native TPV134R gene is cloned into a baculovirus expression system, it is expressed as a non-secreted protein. As described in WO 2007/149566, analysis of the protein sequence using the SignalP program (available from the Center for Biological Sequence Analysis at the Technical University of Denmark), found that the N-terminal hydrophobic sequence had low probability of (i) being cleaved and (ii) functioning as a secretory signal sequence. Accordingly, the sequence coding for the 18 N-terminal amino acids of the 1348 protein may be replaced by sequence encoding the first 18 amino acids of the myxoma virus T7 sequence (MDGRLVFLLASLAIVSDA; SEQ ID NO: 12; FIG. 2). Analysis of the myxoma virus T7 sequence (SEQ ID NO: 11) using the SignalP software indicates that these first 18 amino acids are predicted to act as a signal sequence and are further predicted to have a cleavage site between amino acids 18 and 19. The nucleic acid sequences with the signal sequence replaced with the one from myxoma virus T7 are termed Syn-134R (SEQ ID NO: 4) and Syn2-134R (SEQ ID NO: 6), which correspond to Yaba Like Disease Virus (YLDVI 34R) (SEQ ID NOS:2 and 8) and Tanapox 134R (TPV134R) (SEQ ID NOS:1 and 7; FIGS. 1A and 1B), respectively.

In general, the TPV Polypeptides may be produced by transformation or transfection of a suitable host cell with all or part of a cDNA fragment encoding the polypeptide in a suitable expression vehicle. Those skilled in the field of molecular biology will understand that any of a wide variety of expression systems may be used to provide the recombinant protein. The precise host cell used is not critical to the invention. The polypeptide may be produced in a prokaryotic host (e.g., *E. coli*) or in a eukaryotic host (yeast cells, e.g., *Saccharomyces cerevisiae*, insect cells, e.g., Sf21 cells, or mammalian cells, e.g., COS1, COS7, HEK293, NIH 3T3, or HeLa cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual, P. H. Pouwels et al., 1985, Supp. 1987). One preferred expression system is the baculovirus system (using, for example, the vector pBacPAK9 or the vectors described herein) available from Clontech (Palo Alto, Calif.). If desired, this system may be used in conjunction with other protein expression techniques, for example, the myc-tag approach described by Evan et al. (Mol Cell Biol 5:3610-3616, 1985).

Alternatively, a protein is produced by a stably-transfected mammalian cell line. A number of vectors suitable for stable transfection of mammalian cells are available to the public, e.g., see Pouwels et al. (supra)', methods for constructing such cell lines are also publicly available, e.g., in Ausubel et al. (supra}. In one example, cDNA encoding the protein is cloned into an expression vector which includes the dihydrofolate reductase (DHFR) gene. Integration of the plasmid and, therefore, the protein-encoding gene into the host cell chromosome is selected for by inclusion of 0.01-300 mM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR cells, ATCC Accession No. CRL 9096) are among the host cells preferred for DHFR selection of a stably-transfected cell line or DHFR-mediated gene amplification.

Once the recombinant protein is expressed, it is purified or isolated, e.g., using affinity chromatography. In one example, an antibody (e.g., produced as described herein) is attached to a column and used to isolate the protein. Lysis and fractionation of protein-harboring cells prior to affinity chromatography are performed by standard methods (see, e.g., Ausubel et al., supra). In another example, proteins are purified or substantially purified from a mixture of compounds such as an extract or supernatant obtained from cells (Ausubel et al., supra). Standard purification techniques can be used to progressively eliminate undesirable compounds from the mixture until a single compound or minimal number of effective compounds has been isolated.

Once isolated, the recombinant protein can, if desired, be further purified, e.g., by high performance liquid chromatography (see, e.g., Fisher, Laboratory Techniques In Biochemistry And Molecular Biology, eds., Work and Burdon, Elsevier, 1980).

TPV Polypeptides, particularly short protein fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful protein fragments or analogs.

The TPV Polypeptides can be attached to any one of a variety of tags. Tags can be amino acid tags or chemical tags and can be added for the purpose of purification (for example, a 6-histidine tag for purification over a nickel column or a myc tag). Various labels can be used as means for detecting binding of a protein to a second protein, for example, to a chemokine or a chemokine receptor. Polypeptides can also be linked to toxins. Proteins linked to toxins can be used, for example, to target toxic drugs to malignant tumors if the protein has the ability localize to the tumor.

One can also use in the method of the invention a fusion polypeptide comprising a myxoma T7 signal sequence (e.g., amino acids 1-18 of the myxoma virus T7 protein (SEQ ID NO:11)) (FIG. 2) and a heterologous sequence. Desirably, the addition of the T7 sequence increases secretion of the heterologous sequence from the cell (e.g., from any cell described herein or known in the art, such as a mammalian cell) in which it is produced, as compared to in the absence of the sequence. In addition, any functional fragment of the signal sequence can be used (e.g., 1, 2, 3, 4, 5, 6, 7, 8, 9, 10, 11, 12, 13, 14, or 15 amino acids may be deleted from either the N-terminal end or the C-terminal end of the signal sequence shown in FIG. 2. In other embodiments, point mutation, insertions, or deletions may be present in the signal sequence. Such changes can be introduced using molecular biological techniques well known in the art. Any appropriate heterologous protein (e.g., any protein known the art) can be chosen to be used in conjunction with the myxoma T7 sequence.

WO 20074/149566 describes polynucleotides encoding TPV134R and TPV Polypeptides. Such polynucleotides comprise sequences encoding biologically active fragments of TPV134R, splice-site and codon optimized versions of TPV134R, and chimeric TPV134R sequences (e.g. polynucleotides including sequence coding for the mature 19-156 amino acids of TPV134R with a heterologous signal sequence). Such polynucleotides can be generated using molecular biological techniques known in the art.

While it is often possible to express poxvirus proteins in a baculovirus expression system, it is desirable to express such proteins in a mammalian cell. Transient expression of viral genes from certain poxviruses in uninfected mammalian cells can be unexpectedly inefficient. The reasons for poor expression levels can be due to suboptimal codon usage, cryptic splice sites, polymerase II termination sequences, or motifs that lead to mRNA instability. Expression of the poxvirus sequences in mammalian cells may be achieved by introducing two general sets of changes into the Tanapox and Yaba Like Disease Virus (YLDV) 134R sequences. The first set of changes is designed to remove predicted splice sites. The second set of changes introduces silent mutations to introduce codons favorable for mammalian expression. These changes allow for high levels of protein expression from sequences which are otherwise unable to express or express poorly in mammalian systems. Transient expression of individual viral proteins allows for the study of the specific gene products without the complications of the background contributions from the other viral proteins.

Transcripts not normally expressed the nucleus of mammalian cells may contain splice sites which render the sequence unable to expressed efficiently. Processing sequences through software that searches for cryptic splice sites using software available from the Berkeley Drosophila Genome Project (University of California, Berkeley) http://www.friutfly.org/cgi-bin/seq_tools/splice.pl can be used to predict potential splice sites. Other software known in the art (e.g., software described herein) may likewise be used to identify potential or putative splice sites. Such changes can be introduced into the 134R polynucleotide sequences (SEQ ID NO's:4 and 6) to generate the Syn-134R and Syn2-134R, respectively.

A second set of silent mutations can be introduced into the 134R sequence to generate codon optimized versions of the polynucleotides coding for these genes. As poxvirus genes are normally transcribed in the cytoplasm and never encounter the nucleus, there has not been any selection pressure exerted by host cell nucleus-resident pathways. To overcome these expression problems, changes can be introduced into the 134R gene. In one example, the percent $GC_3$ in the 134R gene is increased from under 14% to over 75%.

A nucleic acid molecule or polypeptide is "substantially identical" to a reference molecule if it exhibits at least 50%, 55%, 60%, 65%, 68%, 75%, 85%, 90%, 95%, or 99% identity to the sequence of the reference molecule. For polypeptides, the length of comparison sequences is at least 10, 20, 25, 35, or 50 amino acids. For nucleic acid molecules, the length of comparison sequences is at least 30, 50, 60, 75, 100, or 150 nucleotides.

Two nucleic acid sequences may also be "substantially identical" if they hybridize under high stringency conditions. By "high stringency conditions," the inventors mean conditions that allow hybridization comparable with the hybridization that occurs using a DNA probe of at least 500 nucleotides in length, in a buffer containing 0.5 M $NaHPO_4$, pH 7.2, 7% SDS, 1 mM EDTA, and 1% BSA (fraction V), at a temperature of 65° C., or a buffer containing 48% formamide, 4.8× SSC, 0.2 M Tris-Cl, pH 7.6, 1×Denhardt's solution, 10% dextran sulfate, and 0.1% SDS, at a temperature of 42° C. (These are typical conditions for high stringency northern or Southern hybridizations.) High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually 16 nucleotides or longer for PCR or sequencing and 40 nucleotides or longer for in situ hybridization). The high stringency conditions used in these techniques are well known to those skilled in the art of molecular biology, and examples of them can be found, for example, in Ausubel et al., Current Protocols in Molecular Biology, John Wiley & Sons, New York, N.Y., 1998, which is hereby incorporated by reference.

By "biologically active fragment," the inventors mean a polypeptide fragment of a full length polypeptide that is capable of treating the diseases described here (namely, keratoconjunctivitis sicca, diminished corneal sensitivity, atopic keratoconjunctivitis, vernal keratoconjunctivitis, ocular cicatricial pemphigoid, or blepharitis). By "fragment," the inventors mean at least 10, 30, 50, 60, 80, or 100 contiguous amino acids. Fragments of the TPV Polypeptides described herein can be generated by methods known to those skilled in the art or may result from normal protein processing (e.g., removal of amino acids from the nascent polypeptide that are not required for biological activity or removal of amino acids by alternative mRNA splicing or alternative protein processing events). A nucleotide which is "capable of expressing a polypeptide in a mammalian cell" means a nucleotide which, when operably linked to a promoter or other appropriate regulatory element and introduced into a mammalian cell cultured under conditions allowing for expression, will express the polypeptide encoded by the nucleotide at a level detectable using a method standard in the art (e.g., immunogenic techniques such as western blotting or ILISA or protein staining techniques such as silver staining). "Secreted" means that the expressed polypeptide is secreted from the host cell into the culture medium at a level detectable using a method standard in the art. "Capable of increased expression of a polypeptide in a mammalian cell" refers to a polynucleotide containing at least one (e.g., 2, 5, 10, 20) mutation(s) relative to a reference (e.g., wild-type) sequence which is expressed in a quantity at least 10%, 20%, 30%, 40%, 50%, 75%, 100%, 250%, 500%, 1000%, or 5000% greater than expression of the reference sequence under the same conditions.

"GC₃ content" refers to the proportion or percentage of nucleic acid codons within a coding sequence of a polynucleotide which have a guanine or cytosine at the third nucleic acid position of each codon.

By "splice site" the inventors mean a nucleic acid sequence which causes an mRNA to be cleaved following transcription. The presence of a splice site within the coding sequence of an mRNA transcribed from a DNA molecule (for example, a vector) may decrease or result in no detectable expression of the encoded protein. A "predicted splice site" is a spliced site identified based on homology to known splice sites. Such sites can be identified using software known in the art including the software provided by Reese and Eeckman, Lawrence Berkeley National Laboratory, Genome Informatics Group or the software described in Hebsgaard et al. Nucleic Acids Res 1996, 24:3439-3452, 1996 and Brunak et al., J Mol Biol 220:49-65, 1991 (available from the Center for Biological Sequence Analysis at the Technical University of Denmark at http://www.cbs.dtu.dk/services/NetGene2/).

By a "substantially pure polypeptide" the inventors mean a polypeptide (or a fragment or analog thereof) that has been separated from proteins and organic molecules that naturally accompany it. Typically, a polypeptide is substantially pure when it is at least 60%, by weight, free from the proteins and naturally-occurring organic molecules with which it is naturally associated. In other embodiments, the polypeptide is at least 75%, 80%, 90%, 95%, or 99%, by weight, pure. Purity can be measured by any appropriate method, e.g., by column chromatography, polyacrylamide gel electrophoresis, or HPLC analysis. A polypeptide is substantially free of naturally associated components when it is separated from those proteins and organic molecules that accompany it in its natural state. Thus, a protein that is chemically synthesized or produced in a cellular system different from the cell in which it is naturally produced is substantially free from its naturally associated components. Accordingly, substantially pure polypeptides not only include those derived from eukaryotic organisms, but also those synthesized in expression systems, for example, *E. coli* or other prokaryotes, yeast, or insect cells.

"Mammalian cell" means a eukaryotic cell derived from a mammalian species. "Human mammalian cell" means a eukaryotic cell derived from humans. Examples of mammalian cells include Chinese Hamster Ovary (CHO) cells, PERC-6 cells, HeLA cells, COS7 cells, Hek293 cells, and other suitable cell types known to persons skilled in the art.

"Substantially pure nucleic acid molecule" means a nucleic acid molecule that is free of the components that naturally accompany it. For example, a substantially pure DNA is free of the genes that, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or that exists as a separate molecule (e.g., a cDNA or a genomic or cDNA fragment produced by PCR or restriction endonuclease digestion) independent of other sequences. It also includes a recombinant DNA that is part of a hybrid gene encoding additional polypeptide sequence.

By "vector," the inventors mean a genetically engineered plasmid or virus, derived from, for example, a bacteriophage, adenovirus, retrovirus, poxvirus, herpesvirus, or artificial chromosome, that is used to transfer a polypeptide coding sequence, operably linked to a promoter, into a host cell, such that the encoded peptide or polypeptide is expressed within the host cell. A vector may be a gene therapy vector, i.e., a vector designed to transfer genetic material into the cells of a subject for a therapeutic benefit.

Vectors generally contain regulatory sequences, including promoters, operably linked to the polypeptide coding sequences. A "promoter" is a minimal nucleic acid sequence element sufficient to direct transcription. If desired, constructs of the invention can include promoter elements that are sufficient to render promoter-dependent gene expression controllable in a cell type-specific, tissue-specific, or temporal-specific manner, or inducible by external signals or agents. Such elements can be located in the 5\3', or intron regions of a gene. Sequences are "operably linked" when a gene and one or more regulatory sequences are connected in such a way as to permit gene expression when the appropriate molecules (e.g., transcriptional activator proteins) are bound to the regulatory sequences.

"Greater activity" means having, under a given set of conditions, either the ability to act either more rapidly (e.g., at least 10%, 25%, 50%, 100%, 250%, 500%, 1000%, 5000% more rapidly) or to a greater extent (e.g., at least 10%, 25%, 50%, 100%, 250%, 500%, 1000%, 5000% more) as compared to a reference (e.g., native or wild type 134R protein or human IL-10). For example, a polypeptide with greater activity in phosphorylating STAT3 than human IL-10 would generate either a greater amount of phosphorylated STAT3 or generate phosphorylated STAT3 more rapidly than human IL-10, or both.

Methods of Treatment

The method of the invention comprises administering IL-10 or a TPV Polypeptide to a patient to treat ocular diseases such as keratoconjunctivitis sicca, ocular cicatricial pemphigoid, blepharitis, ocular allergy, or ocular infection, and systemic diseases such as Stevens-Johnson disease, and graft versus host disease.

In one embodiment, the method of the invention may be used to treat keratoconjunctivitis sicca. Keratoconjunctivitis sicca, as used here, refers to dry eye disease, which a patient experiences as chronic dryness of the cornea and conjunctiva. Other symptoms include a sandy-gritty feeling in the eye, burning, irritation, or a foreign-body sensation. Patients suffering from dry eye disease complain of mild to severe symptoms, and those with severe symptoms may experience constant and disabling eye irritation, and develop ocular surface epithelial disease and sight-threatening sterile or microbial corneal ulceration. Although the discomfort of keratoconjunctivitis sicca is often associated with ocular inflammation, it need not be; the only criteria is that the cause of the patient's discomfort is a deficiency in the quantity or quality of tears. This distinguishes the dryness of keratoconjunctivitis sicca from the discomfort—sometimes perceived as dryness—in patients with other ocular disease.

In another embodiment, the method of the invention may be used to treat a patient suffering from diminished corneal sensitivity caused by refractive surgery, such as laser-assisted in situ keratomileusis (LASIK), or other trauma to the eye. Such trauma severs the corneal nerves, resulting in a state of nerve injury; this leads to discomfort, often perceived as dryness, despite that a patient may have normal tear production. Corneal sensitivity, as measured by a Cochet-Bonnet esthesiometer, usually returns to normal after a period of several months, but one can administer the therapeutic proteins of the invention to hasten recovery.

In another embodiment, the method of the invention may be used to treat a patient suffering from ocular allergy, such as atopic keratoconjunctivitis (allergic inflammation of the eye) or vernal keratoconjunctivitis (seasonal inflammation of the eye, usually the result of allergy). In another embodiment, the method of the invention may be used to treat conjunctivitis or keratoconjunctivitis of whatever cause, such as bacterial or viral infection. In another embodiment, the method of the invention may be used to treat ocular symptoms of cicatricial pemphigoid. In another embodiment, the method of the invention may be used to treat uveitis, including anterior, intermediate, and posterior uveitis, and panuveitis.

When administering the therapeutic proteins of the invention to treat conditions of the eye, the proteins may be administered by any means that locally affects the eye, meaning that they may be administered topically or by injection into the eye. The proteins may also be administered systemically.

In another embodiment, the method of the invention may be used to treat Stevens-Johnson disease and graft versus host disease. The therapeutic proteins of the invention may be administered locally to treat Stevens-Johnson disease, such as by topically apply a cream or gel containing the protein. For both Stevens-Johnson disease and graft versus host disease the proteins may also be delivered systemically.

Formulation

The therapeutic proteins of the present invention may be prepared for storage by mixing the protein having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or nonionic surfactants such as TWEEN®, PLURONICS®, or polyethylene glycol (PEG).

It is preferable that an effective amount of buffer be included to maintain the pH from about 6 to about 8, preferably about 7. Buffers used are those known to those skilled in the art, and, while not intending to be limiting, some examples are acetate, borate, carbonate, citrate, and phosphate buffers. Preferably, the buffer comprises borate. An effective amount of buffer necessary for the purposes of this invention can be readily determined by a person skilled in the art without undue experimentation. In cases where the buffer comprises borate, it is preferable that the concentration of the borate buffer be about 0.6%.

In one embodiment of the invention, a tonicity agent to be used. Tonicity agents are used in ophthalmic compositions to adjust the concentration of dissolved material to the desired isotonic range. Tonicity agents are known to those skilled in the ophthalmic art; some examples include glycerin, mannitol, sorbitol, sodium chloride, and other electrolytes. In one embodiment, the tonicity agent is sodium chloride.

In one embodiment of the invention, may a preservative to be used when the composition is intended for multiple use. There may also be reasons to use a preservative in single use compositions depending on the individual circumstances. The term preservative has the meaning commonly understood in the ophthalmic art. Preservatives are used to prevent bacterial contamination in multiple-use ophthalmic preparations, and, while not intending to be limiting, examples include benzalkonium chloride, stabilized oxychloro complexes (otherwise known as Purite®), phenylmercuric acetate, chlorobutanol, benzyl alcohol, parabens, and thimerosal. Preferably, the preservative is benzalkonium chloride (BAK).

Under certain circumstances, a surfactant might be used in any of the compositions related to this invention which are described herein. The term surfactant used herein has the meaning commonly understood in the art. Surfactants are used to help solubilize the therapeutically active agent or other insoluble components of the composition, and may serve other purposes as well. Anionic, cationic, amphoteric, zwitterionic, and nonionic surfactants may all be used in this invention. For the purposes of this invention, it is preferable that a nonionic surfactant, such as polysorbates, poloxamers, alcohol ethoxylates, ethylene glycol-propylene glycol block copolymers, fatty acid amides, alkylphenol ethoxylates, or phospholipids, is used in situations where it is desirable to use a surfactant.

In another embodiment, a chelating agent may be used. The term chelating agent refers to a compound that is capable of complexing a metal, as understood by those of ordinary skill in the chemical art. Chelating agents are used in ophthalmic compositions to enhance preservative effectiveness. While not intending to be limiting, some useful chelating agents for the purposes of this invention are edetate salts, like edetate disodium, edetate calcium disodium, edetate sodium, edetate trisodium, and edetate dipotassium.

EXAMPLES

The method of the invention is illustrated by the following examples.

The mouse model of Dry Eye has been a valuable tool for dissecting the immunopathogenic mechanisms of disease. In brief, mice exposed to desiccating stress display rapid and coordinated upregulation of proinflammatory cytokines that precedes autoreactive CD4+ T cell activation. By 5 days post-DS a mixed population of infiltrating inflammatory cells including CD4+ T cells (Th1 and Th17) are detected within the ocular surface tissues, along with elevated levels of Th1- and Th17-derived cytokines, IFN-$\gamma$ and IL-17. Accumulation of T cells and their derivatives correlates with decreased Goblet cell density in the conjunctiva, epithelial cell apoptosis, increased corneal permeability and squamous metaplasia of the corneal surface (Niederkorn et al, 2006; de Paiva 2007, 2009).

Topical treatment with recombinant IL-10 attenuated activation of pathogenic T cells and inhibited the development of experimental Dry Eye. Mice exposed to desiccating stress were treated topically with recombinant mouse IL-10 (100 ng/5 µl/eye/BID) (Millipore #IL020 Lot #LV1395267); following 5 days of stress CD4+ T cells were isolated and $5 \times 10^6$ cells were adoptively transferred to nude recipient mice to assess autoreactive T cell activation.

Figure 4:
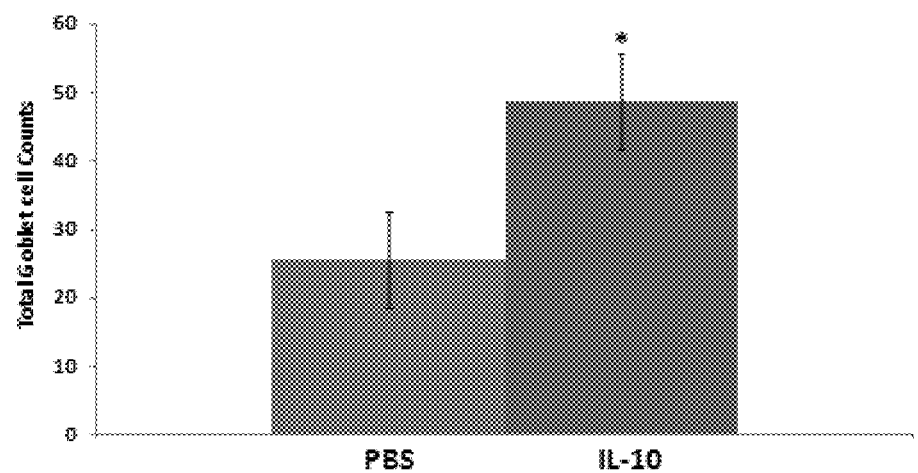

Nude recipients of CD4+ T cells from mice exposed to desiccating stress in the presence of rIL-10 displayed a significant ($p \leq 0.05$) reduction in the number of infiltrating CD4+ T cells within the ocular surface tissues (Lid, meibomian gland—MG, conjunctiva—conj) (Lid: 6.2±0.7, MG: 3.1±0.4, conj: 2.0±0.6) compared to mice treated with vehicle alone (Lid: 24.8±2.5, MG: 22.8±4.4, conj: 26±4.6) (FIG. 3). Furthermore, these mice displayed a significant ($p \leq 0.05$)

preservation of the total number of Goblet cells within the conjunctiva (48.8±7.0); by contrast, mice receiving vehicle alone displayed a dramatic loss of Goblet cells (25.6±8.7) (FIG. 4). Collectively, these data indicate that topical application of full length recombinant IL-10 inhibits generation of autoreactive CD4+ T cells and preserves the integrity of the ocular surface tissues during the development of experimental Dry Eye and argues that this approach a viable therapeutic strategy to reduce the signs and symptoms of chronic T cell-mediated Dry Eye in humans.

In another experiment, the inventors assed the efficacy of the polypeptide of SEQ ID NO:9. The polypeptide was tested using the mouse model of dry eye. Female C57BL/6 mice (6-8 wk old) were purchased from Taconic Farms (Oxnard, Calif.), rested for 7 days, and then dosed topically with 100 ng/5 μl/eye of the polypeptide, TID, for three days prior to, and everyday after induction of experimental dry eye. Experimental dry eye was induced by exposing mice to desiccating stress (DS) in perforated cages with constant airflow from fans positioned on both sides and room humidity maintained at 30-35%. Injection of scopolamine hydrobromide (0.5 mg/0.2 ml; Sigma-Aldrich, St. Louis) was administered three times a day (08:00, 12:00 and 17:00 hr) on alternating hind-flanks to augment disease. DS was induced for 10 consecutive days, and then mice were euthanized and tissues were collected for analysis. The therapeutic efficacy of the polypeptide was evaluated by analyzing: i) tear proinflammatory cytokine levels, i) inflammatory cell infiltration within the cornea, conjunctiva and lacrimal glands, and iii) goblet cell preservation within the conjunctiva. The results showed that the polypeptide of SEQ ID NO:9 reduced tear levels of the proinflammatory cytokines IL-1β, IL-6 and IL-12 relative to vehicle.

What is claimed is:

1. A method for the treatment of an ocular condition selected from keratoconjunctivitis sicca and diminished corneal sensitivity, the method comprising administering to a patient having the condition a composition comprising a polypeptide comprising the amino acid sequence of SEQ ID NO:9.

2. The method of claim 1 wherein the polypeptide comprises an amino acid sequence that is at least 95% identical to SEQ ID NO:9.

3. The method of claim 2, wherein the polypeptide comprises an amino acid sequence that is at least 99% identical to SEQ ID NO:9.

4. The method of claim 1, wherein the polypeptide is substantially pure.

5. The method of claim 1, wherein the polypeptide is administered topically to the eye.

6. The method of claim 1, wherein the polypeptide is administered by injecting it into the eye.

7. The method of claim 1, wherein the ocular condition is keratoconjunctivitis sicca.

8. The method of claim 1, wherein the ocular condition is diminished corneal sensitivity.

* * * * *

UNITED STATES PATENT AND TRADEMARK OFFICE
CERTIFICATE OF CORRECTION

PATENT NO. : 8,491,912 B2
APPLICATION NO. : 13/161964
DATED : July 23, 2013
INVENTOR(S) : Michael E. Stern et al.

Page 1 of 1

It is certified that error appears in the above-identified patent and that said Letters Patent is hereby corrected as shown below:

On the Title Page, in Item (56), under "OTHER PUBLICATIONS", in column 2, line 8, delete "poxvius"," and insert -- poxvirus", --, therefor.

On the Title Page, in Item (56), under "OTHER PUBLICATIONS", in column 2, line 13, delete "De Paiva et a1," and insert -- De Paiva et al, --, therefor.

In the Specification

In Column 5, line 31, delete "1348" and insert -- 134R --, therefor.

Signed and Sealed this
Twenty-second Day of October, 2013

Teresa Stanek Rea
*Deputy Director of the United States Patent and Trademark Office*